United States Patent [19]

Laufenberg et al.

[11] Patent Number: 5,420,317
[45] Date of Patent: May 30, 1995

[54] OLEFINICALLY UNSATURATED ADDUCTS OF PROPYLENE WITH POLYUNSATURATED FATTY ACID OR FATTY ACIDS ESTERS, A PROCESS FOR THEIR PRODUCTION AND THEIR USE

[75] Inventors: Alfred Laufenberg, Dormagen; Arno Behr, Duesseldorf, both of Germany

[73] Assignee: Henkel Kommanditgesellschaft auf Aktien, Duesseldorf, Germany

[21] Appl. No.: 915,844
[22] PCT Filed: Jan. 16, 1991
[86] PCT No.: PCT/EP91/00052
§ 371 Date: Jul. 24, 1992
§ 102(e) Date: Jul. 24, 1992
[87] PCT Pub. No.: WO91/11427
PCT Pub. Date: Aug. 8, 1991

[30] Foreign Application Priority Data

Jan. 24, 1990 [DE] Germany .......... 40 02 008.8

[51] Int. Cl.$^6$ .............................................. C11C 3/06
[52] U.S. Cl. .................................. 554/163; 554/162; 554/165
[58] Field of Search ................ 554/163, 165, 162

[56] References Cited

U.S. PATENT DOCUMENTS

| | | | |
|---|---|---|---|
| 3,636,122 | 1/1972 | Cramer et al. | 260/680 |
| 3,734,859 | 5/1973 | Ward | 252/108 |
| 3,753,968 | 8/1973 | Ward | 260/97.6 |
| 3,966,798 | 6/1976 | Intille et al. | 260/486 |
| 4,318,860 | 3/1982 | Hsu et al. | 554/162 |
| 4,371,469 | 2/1983 | Foglia et al. | 554/161 |
| 4,973,431 | 11/1990 | Struve et al. | 554/141 |

FOREIGN PATENT DOCUMENTS

| | | |
|---|---|---|
| 10807 | 1/1983 | European Pat. Off. . |
| 206367 | 4/1986 | European Pat. Off. . |
| 0206367 | 12/1986 | European Pat. Off. . |
| 2016133 | 12/1970 | Germany . |
| 2253930 | 5/1974 | Germany . |

OTHER PUBLICATIONS

Radical Addition of Methyl Acetoxy Acetate to Olefins and Pyrolysis of the Adducts Yu. N. Ogibin, G. I. Nikishin and L. M. Ilina Feb. 1967.
Fat. Sci. tech., 1, 1, 1988, pp. 1–5.
Fat. Sci. Tech., 1989, pp. 18–23.
Biomed. Mass Spectrom, A. Smith et al., pp. 347–349 1979.
Journal of Molecular Catalysis, 22, 1984, pp. 363–365.
Comprehensive Organometallic Chem., G. Wilkinson (ed.), pp. 414–429 1982.

*Primary Examiner*—José G. Dees
*Assistant Examiner*—Samuel Barts
*Attorney, Agent, or Firm*—Wayne C. Jaeschke; John E. Drach; Henry E. Millson, Jr.

[57] ABSTRACT

Olefinically unsaturated adducts of propylene on polyunsaturated fatty acids with 18 to 22 carbon atoms or on esters of these fatty acids with $C_1$–$C_{36}$ alkanols in molar ratios of propylene to fatty acids or fatty acid esters in the range from 1:1 to 2:1, obtainable by reacting the fatty acids or fatty acid esters with propylene at elevated temperature and pressure in the presence of compounds of the transition metals Ru, Rh, Pd, Ir and Pt as catalysts to form an olefinically unsaturated adduct.

12 Claims, No Drawings

OLEFINICALLY UNSATURATED ADDUCTS OF PROPYLENE WITH POLYUNSATURATED FATTY ACID OR FATTY ACIDS ESTERS, A PROCESS FOR THEIR PRODUCTION AND THEIR USE

BACKGROUND OF THE INVENTION

1. Field of the Invention

This invention relates to olefinically unsaturated adducts of propylene with polyunsaturated $C_{18-22}$ fatty acids or esters thereof with $C_{1-36}$ alkanols in molar ratios of propylene to the fatty acids or fatty acid esters of 1:1 to 2:1 obtainable by reaction of the fatty acids or fatty acid esters with propylene at elevated temperature and elevated pressure in the presence of compounds of transition metals from the group consisting of Ru, Rh, Pd, Ir and Pt as catalysts.

2. Statement of Related Art

Fatty acids branched in the alkyl chain of the Guerbet acid type, obtainable by "guerbetization" of the corresponding fatty alcohols and oxidation of the Guerbet alcohols to the corresponding acids, are technologically interesting intermediate products because they, or their alkyl esters, have distinctly reduced pour points by comparison with the corresponding unbranched isomers. However, the production of Guerbet acids is technologically complicated and can only be carried out with unsatisfactory yields. Accordingly, there has been no shortage of attempts to produce corresponding fatty acid derivatives branched in the alkyl chain from fatty acids or esters thereof. A typical example of this is the layer-silicate-catalyzed dimerization of fatty acids. Unfortunately, considerable quantities of trimeric fatty acids and methyl-branched fatty acids, so-called isofatty acids, are also formed in this reaction. Another, albeit complicated, process gives branched fatty acid derivatives from conjuene fatty acids in the trans-trans form with activated dienophiles under the conditions of a Diels-Alder reaction; for example, a branched $C_{21}$ dicarboxylic acid can be obtained in this way from linoleic acid and acrylic acid, of cf. U.S. Pat. No. 3,734,859, U.S. Pat. No. 3,753,968, DE-B 2 253 930. Other branched fatty acid derivatives have been obtained by thermal or acid-catalyzed addition of activated enophiles onto unsaturated fatty acid derivatives. For example, maleic anhydride can be added onto oleic acid in the presence of an acid as catalyst in yields of up to 70%, cf. Fat. Sci. Technol., 1, 1 (1988). However, the presence of more than one carboxyl group in the reaction products mentioned above has often proved to be troublesome.

Finally, attempts have also been made to add saturated hydrocarbons onto fatty acids by heat-initiated radical addition of saturated hydrocarbons onto fatty acids. The addition of cyclohexane onto oleic acid methyl ester at 340° C./200 bar gives alkyl-branched fatty acids with 70% selectivity, but in a yield of only 2.8%, cf. J. O. Metzger et al., Fat. Sci. Technol. 1 (1989), 18.

DESCRIPTION OF THE INVENTION

The present invention is directed to the provision of olefinically unsaturated adducts of propylene with polyunsaturated fatty acids of the type mentioned at the beginning which can be readily obtained in high yields. The compounds provided in accordance with the invention are new products which, for example, differ in their chain length alone from the naturally occurring ethyl-branched fatty acids containing a total of 12 to 18 carbon atoms described in A. Smith et al. Biomed. Mass Spectrom., 6 (8), 347–349.

Suitable starting products for the production of the olefinically unsaturated adducts according to the invention are unsaturated fatty acids containing 18 to 22 carbon atoms and more than one olefinic double bond, such as linoleic acid, isomerized linoleic acid containing conjugated double bonds (so-called $C_{18}$: 2-conjuene fatty acid), linolenic acid, arachidonic acid, docosadienoic acid, docosahexaenoic and eicosapentaenoic acid, which can be obtained in the form of technical mixtures with other fatty acids from renewable natural raw materials, for example from sunflower oil, tall oil or fish oil. As usual in oleochemistry, these polyunsaturated fatty acids are generally not used in the form of their pure compounds, but rather in the form of technical mixtures for the preparation of the adducts according to the invention. The abovementioned fatty acids are preferably used not only as such, but also in the form of their esters with $C_{1-36}$ alkanols, more particularly with $C_{1-4}$ alkanols. Typical examples of such alkanols for the formation of esters with the fatty acids mentioned above are methanol, ethanol, propanol, butanol, pentanol, hexanol, octanol, decanol, dodecanol, tetradecanol, hexadecanol, octadecanol and higher fatty alcohols or fatty alcohol derivatives containing up to 36 carbon atoms, for example $C_{36}$ Guerbet alcohols.

According to the invention, the polyunsaturated fatty acids or fatty acid esters mentioned above are added onto propylene at elevated temperature and pressure in the presence of compounds of transition metals from the group consisting of Ru, Rh, Pd, Ir and Pt.

The following are typical examples of catalysts suitable for use in accordance with the invention:

$RhCl_3 \cdot 3H_2O$
$RhBr_3 \cdot 3H_2O$
$[(C_2H_4)_2RhCl]_2$
$Rh(NO_3)_3 \cdot 2H_2O$
$Rh(OOCCH_3)_2 \cdot 2H_2O$
$Rh(acetylacetonate)_3$
$RhF_3 \cdot 6H_2O$
$RhI_3$
$Rh(CN)_3 \cdot 3H_2O$
$Rh_2(SO_4)_3$
$Rh_2(CO_3)_3$
$[(1.5\text{-cyclooctadiene})RhCl]_2$
$[(C_2H_4)_2Rh(acetylacetonate)]$
$[(1.3\text{-butadiene})RhCl]_2$
cyclopentadienyl-olefin complexes, such as $[(n\text{-}C_5H_5)Rh\text{-}(C_2H_4)_2]$.

Where the catalysts suitable for use in accordance with the invention are present in anhydrous form, it may be advisable to add a small quantity of water to the reaction mixture.

The catalysts suitable for use in accordance with the invention are known as such for the addition of ethylene onto alkadienes, cf. U.S. Pat. No. 3,636,122; M. Bochmann et al., Journal of Molecular Catalysis, 22 (1984), 363–365; G. Wilkinson (Ed.), Comprehensive Organometallic Chemistry, pages 414–429, Pergamon Press (1982); A.C.L. Su, Advances in Organometallic Chemistry, Vol. 17, pages 271–283. However, these publications, to the subject matter of which reference is hereby specifically made, are not concerned with the addition of alkenes onto fatty acids or fatty acid derivatives or other fatty compounds.

Other catalysts suitable for use in accordance with the invention are, for example,
$PdCl_2$
$PtCl_2$
$IrCl_3$
$OsCl_3$
$Ru(acetylacetonate)_3$.

Mixtures of 1:1 and 2:1 adducts of propylene with the fatty acids or fatty acid esters are generally formed with the catalysts suitable for use in accordance with the invention. However, the percentage contents of the various adducts can be varied by modifying the reaction conditions, such as pressure, temperature and reaction time. However, if suitable phosphine or phosphite ligands, for example
$P(C_4H_9)_3$
$P(OC_4H_9)_3$
$P(C_6H_5)_3$
$P(OC_6H_5)_3$
or other ligands known from the prior art just discussed and from DE-B 20 16 133, are added to the reaction mixture in addition to the catalysts, the composition of the adduct mixtures may be selectively influenced. Similar effects can be obtained to an extent by addition to the reaction system of promoters such as LiCl, $FeCl_3$ or $AgBF_4$ which are also known as such from the last-mentioned prior art.

The structure of the olefinically unsaturated adducts according to the invention is not uniform. In the case of linoleic acid (or the $C_{18}$ conjuene fatty acid derived therefrom), it could be shown that the addition of the first propylene molecule takes place between the 9 and 12 positions of the carbon chain of the linoleic acid, the 1:1 adduct having the same number of double bonds as the fatty acid used as starting material. However, the position of the double bonds is uncertain. In no case are the double bonds further than 4 carbon atoms from the branching and, basically, they are in the $\alpha,\delta$- or $\alpha,\gamma$-position to one another. The second propylene molecule is then added onto a double bond situated in the branching. It may be assumed that at least some of the adducts obtained in accordance with the invention have one of the structures shown below:

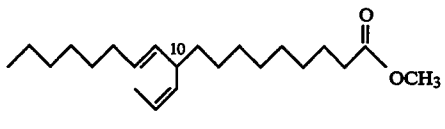

1:1 Propene adduct

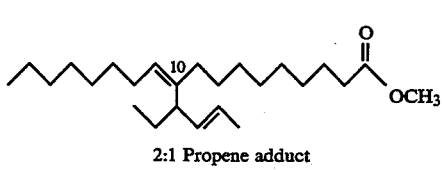

2:1 Propene adduct

In one advantageous embodiment of the invention, the polyunsaturated fatty acids optionally used in the form of their esters contain from 2 to 5 and, more particularly, from 2 to 3 olefinic double bonds.

In another advantageous embodiment of the invention, the adducts are obtained under a propylene pressure in the range from 5 to 40 bar and at a temperature in the range from 50° to 140° C., the reaction optionally being carried out in the presence of inert organic solvents, such as hexane, chloroform or the like.

In another advantageous embodiment of the invention, the catalysts are used in a quantity of 0.02 to 2 mol-%, based on fatty acids or fatty acid esters.

Rhodium compounds are advantageously used as the catalysts, rhodium compounds from the group consisting of $RhCl_3$ and $RhBr_3$ (including hydrates thereof) and $[(C_2H_4)_2\text{-}RhCl]_2$ preferably being used as catalysts.

The invention also relates to a process for the production of olefinically unsaturated adducts of propylene with polyunsaturated fatty acids containing 18 to 22 carbon atoms or esters thereof with $C_{1-36}$ alkanols in molar ratios of propylene to the fatty acids or fatty acid esters of 1:1 to 2:1 having the features described above.

The olefinically unsaturated adducts according to the invention are suitable as starting products for the production of saturated, branched fatty acids containing 21 to 28 carbon atoms or esters thereof with $C_{1-36}$ alkanols which may be used, for example, in cosmetic formulations and more particularly in lubricants.

The invention is illustrated by the following Examples.

EXAMPLE 1

In a 75 ml autoclave, 8.2 g of a technical fatty acid mixture containing 67.8% by weight linoleic acid methyl ester (19 mmol), 100 mg $RhCl_3.3H_2O$ and 10 ml chloroform were reacted for 20 h at 100° C. in the presence of excess propene. 1:1 Adducts were obtained in a yield of 27.6% (as determined by gas chromatography), based on linoleic acid methyl ester.

EXAMPLE 2

In a 75 ml autoclave, 8.2 g of a technical fatty acid containing 56.0% $C_{18}:2$ conjuene acids, 100 mg $RhCl_3.3H_2O$ and 10 ml hexane were reacted for 20 h at 100° C. in the presence of an excess of propylene. 1:1 Adducts were obtained in a yield of 70.5%, based on conjuene fatty acid.

EXAMPLE 3

In a 75 ml autoclave, a technical fatty acid methyl ester mixture containing 62.4% conjugated $C_{18}:2$ fatty acid methyl ester, 100 mg $RhCl_3.3H_2O$ and 10 ml hexane were reacted for 20 h at 100° C. in the presence of an excess of propylene. 1:1 Adducts were obtained in a yield of 58.5%, based on conjugated fatty acid methyl ester.

EXAMPLE 4

In a 1 liter stirred autoclave equipped with a turbine stirrer, 300 g of a fatty acid methyl ester according to Example 3, 3.0 g $RhCl_3.3H_2O$ and 350 ml hexane were reacted for 20 h at 100° C. in the presence of an excess of propylene. 1:1 Adducts were obtained in a yield of 98.2%, based on conjugated fatty acid methyl ester.

EXAMPLE 5

301 g of a fatty acid methyl ester mixture containing 60.3% $C_{18}:2$ conjuene methyl ester (197 g; 0.76 mol), 6.2% linoleic acid methyl ester and 24.4% oleic acid methyl ester, 881.6 mg (3.35 mmol) $RhCl_3.3H_2O$ (263.5 g/mol) and 350 ml hexane were introduced into a 1 liter stirred autoclave equipped with a turbine stirrer. Approx. 100 g propene were then incorporated by condensation. The reaction mixture was stirred for 20 h at 100° C. Propylene adducts were obtained in a yield of 91.9%, based on conjuene fatty acid ester, being made up of 85.2% 1:1 adducts and 6.7% 2:1 adducts.

What is claimed is:

1. Olefinically unsaturated adducts of propylene with polyunsaturated $C_{18-22}$ fatty acids or esters thereof esterified with $C_{1-36}$ alkanols produced by the process comprising reacting unsaturated fatty acids containing 18 to 22 carbon atoms and more than one olefinic bond or esters thereof esterified with $C_{1-36}$ alkanols with propylene at a temperature of from about 50° C. to about 140° C. and at a pressure of from about 5 to about 40 bar in the presence of transition metal compounds selected from the group consisting of Ru, Rh, Pd, Ir, or Pt wherein the molar ratio of propylene to fatty acid or fatty acid ester is from about 1:1 to about 2:1 to form an olefinically unsaturated adduct.

2. The olefinically unsaturated adducts as claimed in claim 1 wherein said fatty acids containing 18 to 22 carbon atoms also contain from 2 to 5 olefinic bonds.

3. The olefinically unsaturated adducts as claimed in claim 2 wherein said fatty acids containing 18 to 22 carbon atoms also contain from 2 to 35 olefinic bonds.

4. The olefinically unsaturated adducts as claimed in claim 1 wherein the amount of said transition metal compound is from about 0.02 to about 2 mole % based on fatty acid or fatty acid ester.

5. The olefinically unsaturated adducts as claimed in claim 1 wherein said transition metal compound is a rhodium compound.

6. The olefinically unsaturated adducts as claimed in claim 5 wherein said rhodium compound is $RhCl_3$, $RhBr_3$, hydrates of $RhBr_3$, or $((C_2H_4)_2RhCl)_2$.

7. A process for producing olefinically unsaturated adducts of propylene with polyunsaturated $C_{18-22}$ fatty acids or esters thereof esterified with $C_{1-36}$ alkanols which comprises reacting at least one unsaturated fatty acid containing 18 to 22 carbon atoms and more than one olefinic bond or an ester thereof esterified with a $C_{1-36}$ alkanol with propylene at a temperature of from about 50° C. to about 140° C. and at a pressure of from about 5 to about 40 bar in the presence of a catalyst consisting essentially of at least one transition metal compound selected from the group consisting of Ru, Rh, Pd, It, and Pt, and optionally a phosphine or phosphite ligand and/or an inorganic promoter, wherein the molar ratio of propylene to fatty acid or fatty acid ester is from about 1:1 to about 2:1 to form at least one olefinically unsaturated adduct.

8. The process of claim 7 wherein said fatty acids containing 18 to 22 carbon atoms also contain from 2 to 5 olefinic bonds.

9. The process as claimed in claim 7 wherein said fatty acids containing 18 to 22 carbon atoms also contain from 2 to 35 olefinic bonds.

10. The process as claimed in claim 7 wherein the amount of said transition metal compound is from about 0.02 to about 2 mole % based on fatty acid or fatty acid ester.

11. The process as claimed in claim 7 wherein said transition metal compound is a rhodium compound.

12. The process as claimed in claim 7 wherein said rhodium compound is $RhCl_3$, $RhBr_3$, hydrates of $RhBr_3$, or $((C_2H_4)_2RhCl)_2$.

* * * * *